United States Patent
Smith et al.

(10) Patent No.: US 7,244,259 B2
(45) Date of Patent: Jul. 17, 2007

(54) GUIDE FOR SURGICAL DEVICE FOR THE TREATMENT OF URINARY INCONTINENCE

(75) Inventors: Daniel J. Smith, Dayton, NJ (US); Jonathan B. Gabel, Randolph, NJ (US)

(73) Assignee: Ethicon, Inc., Somerville, NJ (US)

( * ) Notice: Subject to any disclaimer, the term of this patent is extended or adjusted under 35 U.S.C. 154(b) by 441 days.

(21) Appl. No.: 10/699,045

(22) Filed: Oct. 31, 2003

(65) Prior Publication Data

US 2005/0096667 A1    May 5, 2005

(51) Int. Cl.
*A61F 2/00* (2006.01)
(52) U.S. Cl. .................... 606/119; 600/29
(58) Field of Classification Search ............. None
See application file for complete search history.

(56) References Cited

U.S. PATENT DOCUMENTS

| | | | |
|---|---|---|---|
| 5,785,640 A * | 7/1998 | Kresch et al. | 600/29 |
| 5,951,525 A * | 9/1999 | Thorne et al. | 604/198 |
| 6,605,097 B1 | 8/2003 | Lehe et al. | |
| 6,638,211 B2 | 10/2003 | Suslian et al. | |

FOREIGN PATENT DOCUMENTS

| WO | WO 98/22017 A2 | 5/1998 |
|---|---|---|
| WO | WO 98/40114 A1 | 9/1998 |

OTHER PUBLICATIONS

Nickel, R.F. et al., "Evaulation of a Transpelvic Sling Procedure With and Without Colposuspension for Treatment of Female Dogs with Refractory Urethral Sphincter Mechanism Incompetence," Veterinary Surgery 27:94-101 (1998).

International Search Report dated Feb. 7, 2005, for corresponding application PCT/US2004/034808.

* cited by examiner

*Primary Examiner*—Alvin J. Stewart
*Assistant Examiner*—Christopher D Prone (57) ABSTRACT

A surgical guide and its use in medical procedures such as to treat female urinary incontinence are provided. The guide preferably includes a stem portion having a proximal end and a distal end and a cross-sectional shape having a recess therein along its length and first and second extension portions extending outwardly from opposites sides of the distal end of the stem portion. Each of said first and second extension portions further include a stationary portion that is fixedly coupled to the stem portion and a movable portion that is movably coupled to the stationary portion. The movable portions are movable relative to the respective stationary portions between a first position wherein the stem portions extends beyond the extension portions by a first distance and a second position wherein the stem portion extends beyond the extension portions by a second distance that is greater than the first distance.

13 Claims, 7 Drawing Sheets

GUIDE FOR SURGICAL DEVICE FOR THE TREATMENT OF URINARY INCONTINENCE

BACKGROUND OF THE INVENTION

1. Field of the Invention

The present invention relates generally to devices and methods for the treatment of female urinary incontinence, and more particularly, to a guide to be used in conjunction with such devices and methods.

2. Background Discussion

Women account for more than 11 million of incontinence cases. Moreover, a majority of women with incontinence suffer from stress urinary incontinence (SUI). Women with SUI involuntarily lose urine during normal daily activities and movements, such as laughing, coughing, sneezing and regular exercise.

SUI may be caused by a functional defect of the tissue or ligaments connecting the vaginal wall with the pelvic muscles and pubic bone. Common causes include repetitive straining of the pelvic muscles, childbirth, loss of pelvic muscle tone, and estrogen loss. Such a defect results in an improperly functioning urethra. Unlike other types of incontinence, SUI is not a problem of the bladder.

Normally, the urethra, when properly supported by strong pelvic floor muscles and healthy connective tissue, maintains a tight seal to prevent involuntary loss of urine. When a woman suffers from the most common form of SUI, however, weakened muscle and pelvic tissues are unable to adequately support the urethra in its correct position. As a result, during normal movements when pressure is exerted on the bladder from the diaphragm, the urethra cannot retain its seal, permitting urine to escape. Because SUI is both embarrassing and unpredictable, many women with SUI avoid an active lifestyle and shy away from social situations.

One device and method for treating female urinary stress incontinence is described in detail in U.S. Pat. No. 5,899,909, which is incorporated herein by reference in its entirety. This patent discloses a surgical instrument comprising a shank having a handle at one end and connecting means at the other end to receive, one at a time, two curved needle-like elements which are connected at one end to one end of a mesh intended to be implanted into the body. In practice, the mesh is passed into the body via the vagina first at one end and then at the other end, at one side and the other, respectively, of the urethra to form a loop around the urethra, located between the urethra and vaginal wall. The mesh is extended over the pubis and through the abdominal wall and is tightened. The mesh ends are cut at the abdominal wall, and the mesh is left implanted in the body. This trans-vaginal procedure is exemplified by the TVT product sold by the Gynecare franchise of Ethicon Inc., a Johnson & Johnson Company, of Somerville, N.J., USA. In this procedure two 5 mm needles pass a PROLENE mesh trans-vaginally and through the abdomen to create a tension-free support around the mid urethra.

Sub-urethral slings have also been place by a different approach, wherein a needle is passed first though the abdominal wall, along the same path as described above, and eventually exiting through the vaginal incision. The tape is then coupled to the needle in some manner, and pulled back through the body from the vaginal incision and out through the abdominal incision. The chosen approach, vaginal or abdominal, will often depend on the preferences of the surgeon.

Yet another approach for implanting a sub-urethral sling has also been recently developed, wherein the implanted sling extends from beneath the urethra, and out through the obturator hole on either side. This "transobturator" procedure may involve inserting an appropriately configured needle from a vaginal incision and subsequently out through the obturator hole, or vice versa. The former technique (an "inside-out" approach) is described in further detail below. With these techniques, it has been found to be desirable to provide some sort of guide element to facilitate the path of the needle and to ensure that the needle does not nick or otherwise injure organs or nerves that are in the vicinity of the passageway of the needle. To this end, known guide elements have consisted simply of a small stainless steel tube, a portion of which has been removed to leave a straight, but C-shaped element. Such guide elements have proven less than optimal, however, as they are difficult to maintain in place without slipping, and don't provide protection against over-insertion which can lead to damage to surrounding tissues and organs. The present invention provides an improved guide device that can be used in conjunction with a transobturator approach for placing a sub-urethral sling.

SUMMARY OF THE INVENTION

These and other features and advantages of the present invention will become apparent from the following more detailed description, when taken in conjunction with the accompanying drawings which illustrate, by way of example, the principles of the invention.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways.

Referring now to FIGS. 1–4, one embodiment of a guide element 100 according to the present invention has a proximal end 103 and a distal end 105, and includes a stem portion 102 and an extension 104 extending outwardly from the stem portion at the distal end. In the illustrated embodiment, the extension 104 includes first and second extension or wing portions 106, 108 extending in substantially opposite directions from the distal end of the device. It is preferred that the extension portions 106, 108 form an angle therebetween of less than 180 degrees, such as the 135 degree angle shown in FIG. 4. Angles between 45 and 180 degrees, however, are also suitable. Any such angle should be toward (or in the direction of) rather than away from the opening O formed by the curved cross-section of the stem portion, as shown. The cross-section of the stem portion extends along the length of the device and has a recess r therein. The recess is preferably curved, having a C-shaped configuration, but any shaped configuration is suitable so long as it has a diameter W sufficient to receive and guide a surgical needle as described further below. In a preferred embodiment, the diameter W is approximately 4.2 mm, which would be suitable for a surgical needle having a diameter of approximately 3.8–5.0 mm. In the illustrated embodiment, the extension portions of the device 100 have a plurality of gripping elements 110 to aid the surgeon in grasping and manipulating the device. These gripping elements may be protrusions or the like, or may be apertures or recesses.

Figure 1:
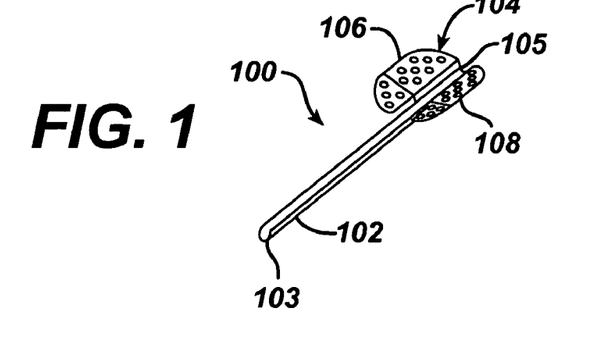
FIG. 1 is a perspective view illustrating a guide device according to the present invention.
Figure 2:
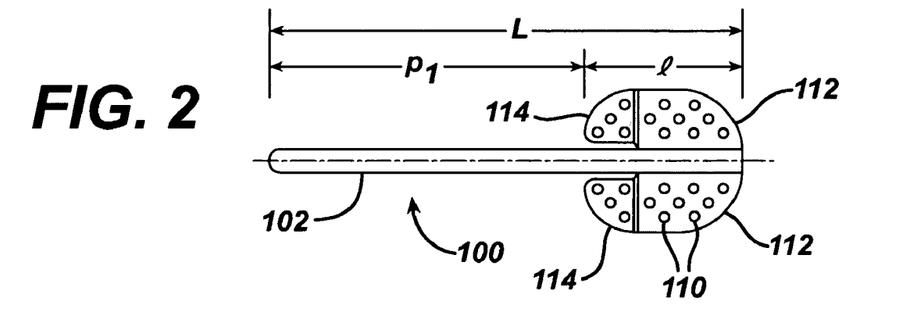
FIG. 2 is a top view illustrating the guide element of FIG. 1.
Figure 3:
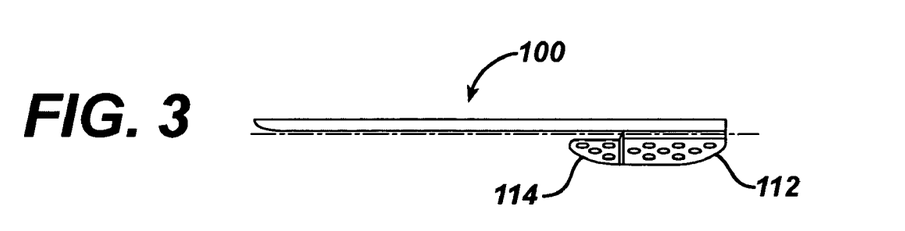
FIG. 3 is a side view illustrating the guide element of FIG. 1.
Figure 4:
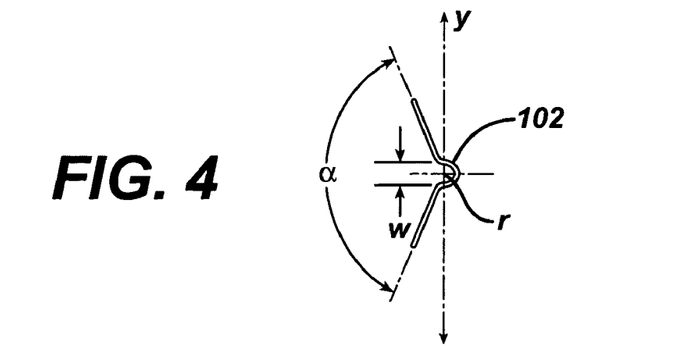
FIG. 4 is a frontal view of the guide element of FIG. 1.

According to one embodiment, the extension portions each are further comprised of a stationary portion 112 that is fixed relative to the stem portion and a movable portion 114 that is movable relative to the stem portion. In the illustrated embodiment, the stationary portions are fixedly secured to the stem portion and the movable portions are movably secured to the stationary portions at one or more hinges 116 (see FIG. 5) having a width t suitable to provide the desired bendability. In a preferred embodiment, the guide is made of stainless steel having a thickness of approximately 0.5 mm. Two hinges 116 are used on each side, each having a width t of approximately 0.7–0.8 mm. The hinges 116 permit the movable portion to move or bend relative to the stationary portion to the position shown in FIG. 5 or in the opposite direction to that shown. An important aspect of this feature is that it readily allows the guide device to be used with any different pelvic structures or size of patient as will be described below. With the movable portions 114 in a first position relative to the stationary portions 112 as shown in FIGS. 2 and 3, the movable portions are essentially extensions of the stationary portions in substantially the same plane. It is not essential that they exist in the same plane, but what is important is that in this position, the stem portion 102 extends beyond, or is clear from, the extension portions for a first distance p1. When the movable portions are moved relative to the stationary portions to a second position such as that shown in FIG. 5, the stem portion extends beyond the extension portions by a second distance p2 that is greater than the first distance p1. This allows flexibility in using the guide element to guide surgical needles through dissected passageways in the body having different lengths, as will be further apparent from the discussion of the surgical method below.

In a preferred embodiment, the overall length L of the device is approximately 90 mm, but any length from approximately 80–120 mm or greater would be suitable. The overall length l of the extension portions is preferably 30 mm, but could be approximately 20–50 mm. The entire device is preferably made of stamped ¼ hard stainless steel having a thickness of approximately 0.5 mm (with approximately 0.25–1.0 m being a suitable range). The proper dimensions of the device will be further appreciated following the discussion below of the medical procedure with which it may be used.

Figure 6:
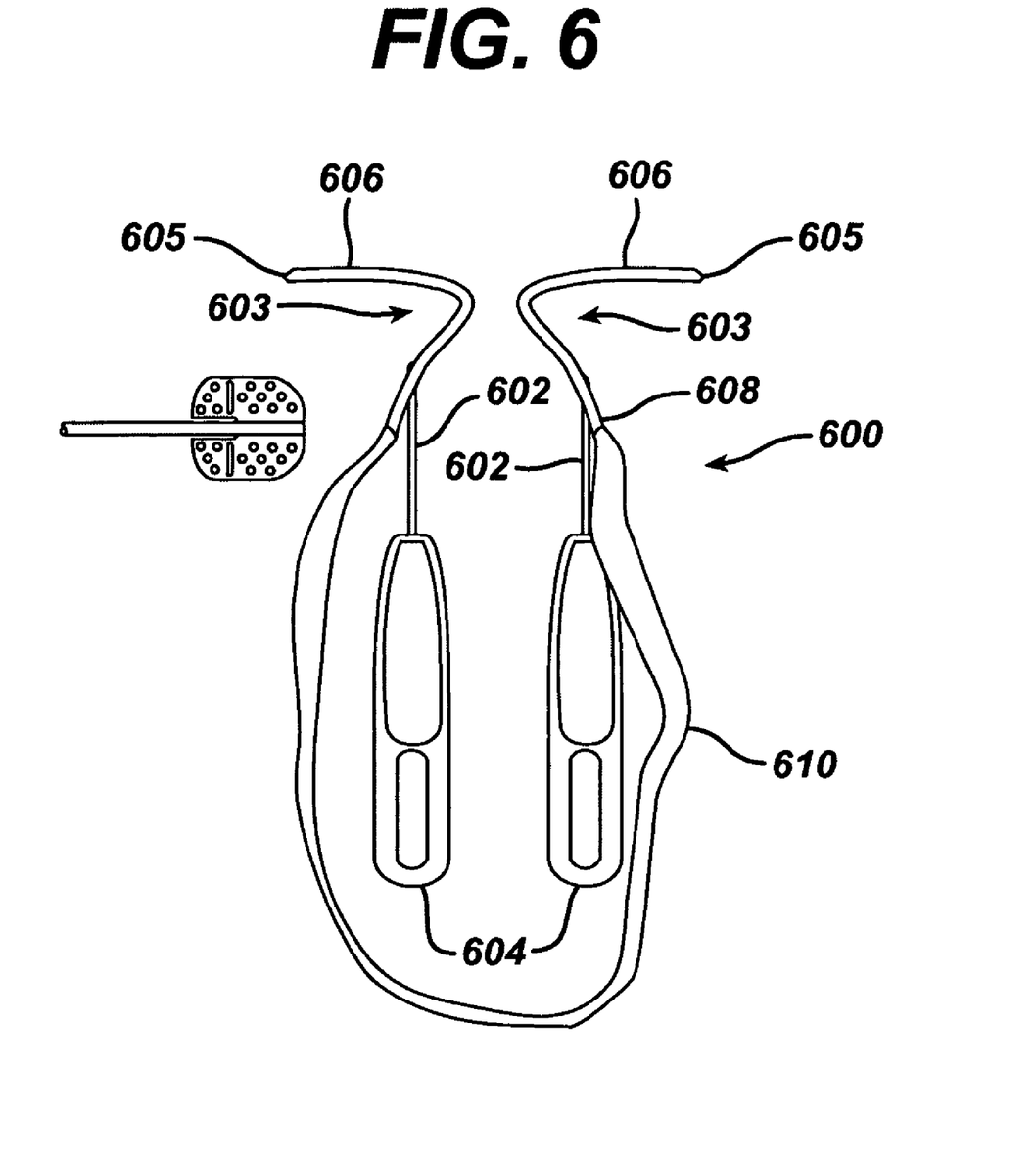
FIG. 6 illustrates an exemplary surgical instrument with which the guide of the present invention can be used.

As indicated above, the guide of the present invention may be used in conjunction with a surgical device and method to place a sub-urethral sling via a pathway that extends through the obturator foramen. In a preferred embodiment, the guide is used in conjunction with a surgical instrument 600 such as that shown in FIG. 6. The surgical instrument 600 consists of two surgical assemblies 603 including two surgical passers 602 secured respectively to two handles 604, and two tube elements 606 having pointed or tissue penetrating distal ends 605 applied over the ends of the surgical passers. The surgical passers (and associated tube elements) are curved and form a somewhat helical shape, and are mirror images of one another so that one is particularly suited for passage through the body on one side of the urethra, whereas the other is particularly suited for passage on the opposite side of the urethra. Proximal ends 608 of the tube elements are coupled to the tape 610 to be implanted. The tape is preferably of knitted mesh construction, such as Prolene® polypropylene mesh (manufactured by Ethicon, Inc. of Somerville, N.J.) having dimensions of approximately ½×18 inches. The tape is also preferably covered by a plastic sheath that overlaps in the middle section so as to be easily removable. Although the illustrated embodiment shows a surgical assembly including surgical passers having tube elements covering their distal ends, it is to be understood that other embodiments consisting of only a surgical passer itself having a pointed or tissue penetrating distal end could also be used in conjunction with the guide of the present invention. Thus, the term "surgical needle" is being used herein to refer to a surgical element having tissue penetrating distal end, regardless of whether being a single element or an assembly.

To perform the procedure, the patient is first placed in the dorsal lithotomy position with the hips hyperflexed over the abdomen, and the bladder emptied. Next, the exit points 702 (FIG. 7a) of the surgical needles through the obturator foramen 707 are marked. A midline incision is then made in the vaginal mucosa 705, and the left and right sides dissected with scissors or the like until it reaches and dissects the obturator membrane.

Figure 5:
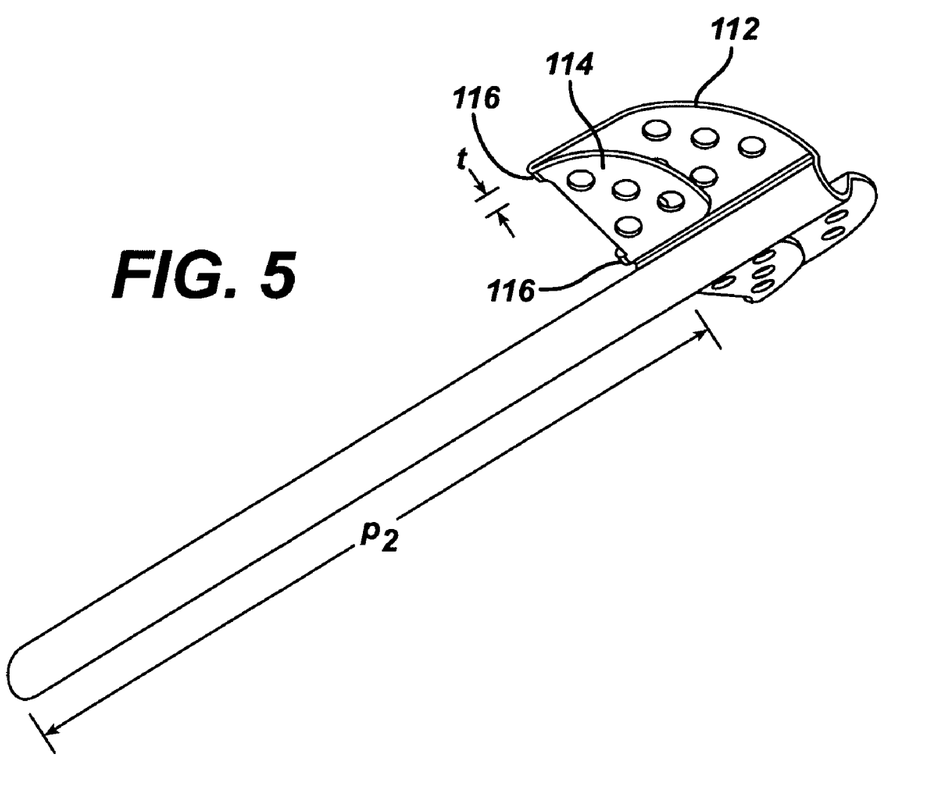
FIG. 5 is a perspective view illustrating the guide device of FIG. 1 with the movable portions of the wings in a bended configuration.
Figure 7A:
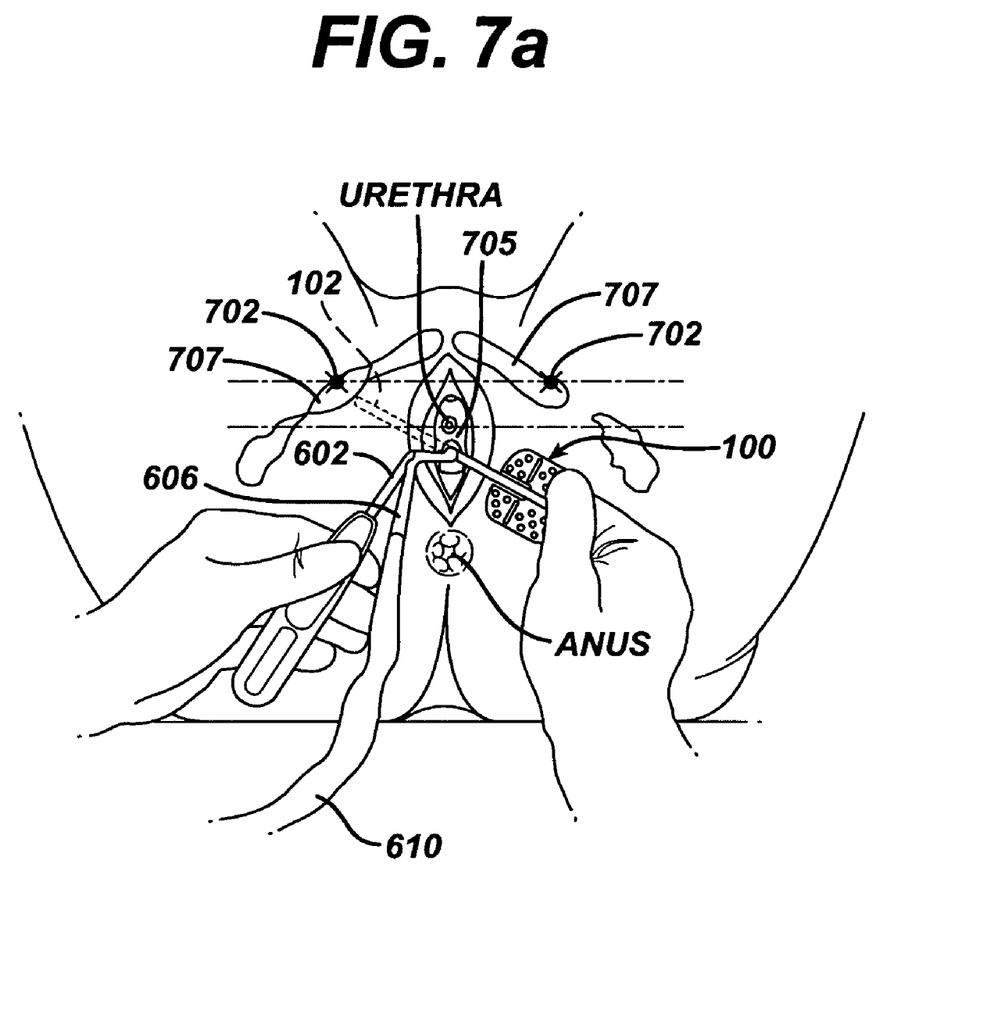
FIGS. 7a, 7b and 8 illustrates steps that may be used in when using the guide element of the present invention to implant a sling.
Figure 7B:
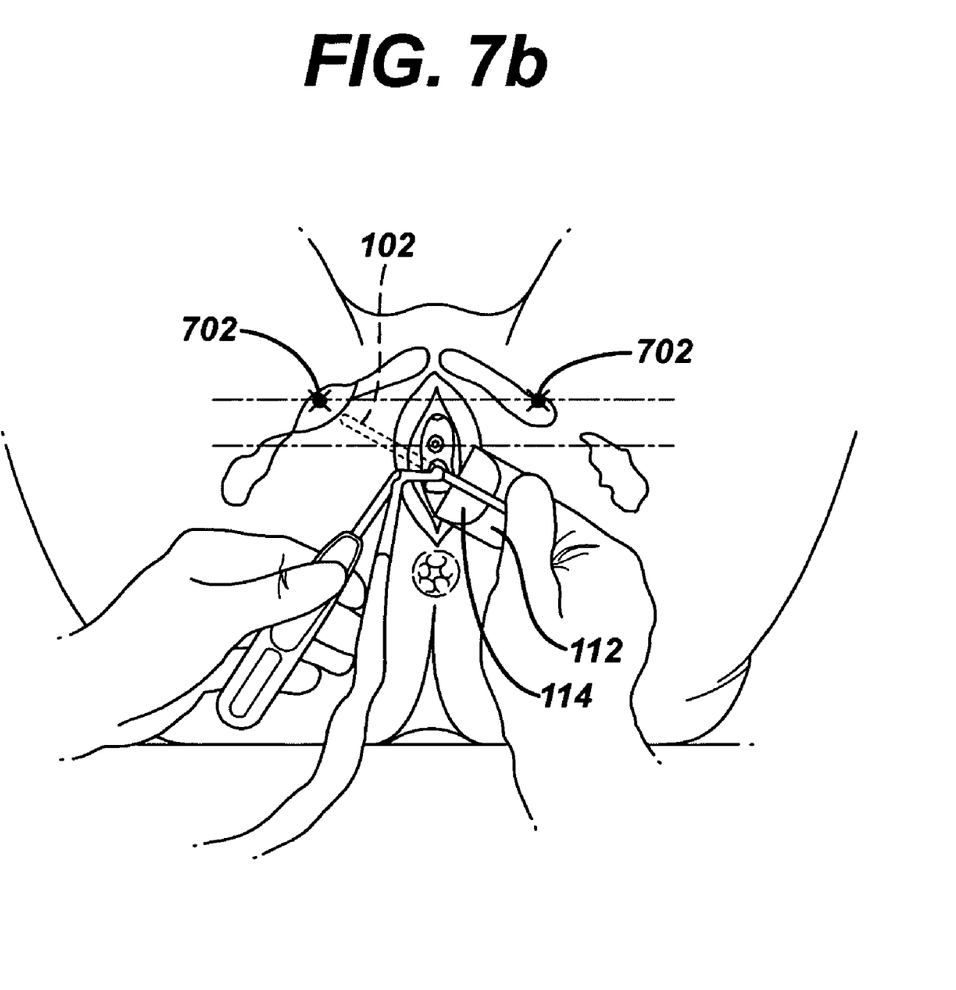

Next, the guide element 100 is inserted as shown in FIG. 7a through the vaginal incision and into the dissected tract until is passes the inferior pubic ramus and enters the opening previously made in the obturator membrane. The extension 104 remains outside the dissected tract, and the open side of the curved or C-shaped stem portion 101 faces laterally outward rather than inward toward the midline of the body. In the illustration of FIG. 7a, the stationary portions 112 and the movable portions 114 of the extension 104 remain in a substantially fixed or planar configuration relative to one another, as the length of the stem portion 102 extending beyond the extension is sufficient to extend the length of the dissected tract. Many patients, however, have a larger pelvic frame or have obese weight conditions such that the length of the dissected tract is longer. Under these circumstances, the movable portion of the extensions can be bent in either direction against the stationary portions as shown in FIG. 5, so that when the guide is inserted (shown in FIG. 7b) the stem portion that extends beyond the extension portion is longer and able to extend the length of the dissected path. Thus, the guide element according to the present invention is easily and readily usable in any patient.

The extension portions provide the added safety of having a "stop" to prevent the guide from accidentally being pushed too far into the body. To fully understand the benefits of the present invention, it is important to recognize that the obturator nerve and vessels are approximately 8.5–9.5 cm away from the entry point of the guide. This nerve and vessels are critical to avoid, as injury thereto could possibly cause paralysis. Thus, for most patients, to ensure safety of the guide element its length (the length that can be inserted) need not exceed approximately 6 cm. However, as indicated above, some patients either have larger pelvic frames, or are obese, rendering a guide length of 6 cm sub-optimal at best. Therefore, using known guides consisting simply of a straight transected cylinder (7 cm+3 cm) suitable to be inserted a full 10 or more cm, a surgeon would either have to always have available multiple guides having different lengths (i.e., one having an insertable length of approximately 6 cm and a second one having an insertable length of approximately 7 cm to accommodate patients with larger pelvic frames or obese patients), or rely on skill in using a single 7 cm round guide which could be inadvertently inserted to an unsafe depth of 7 to 10 cm for all patients. The latter is obviously dangerous and subject to human error, particularly with surgeons that are not highly experienced with the procedure. The former leads to added expense and waste. The guide of the present invention overcomes these problems by providing extensions to protect against over-insertion, (which the earlier invention did not prevent), with the extension having bendable portions for varying the insertable length of the stem to enable safe use in any patient.

Figure 8:
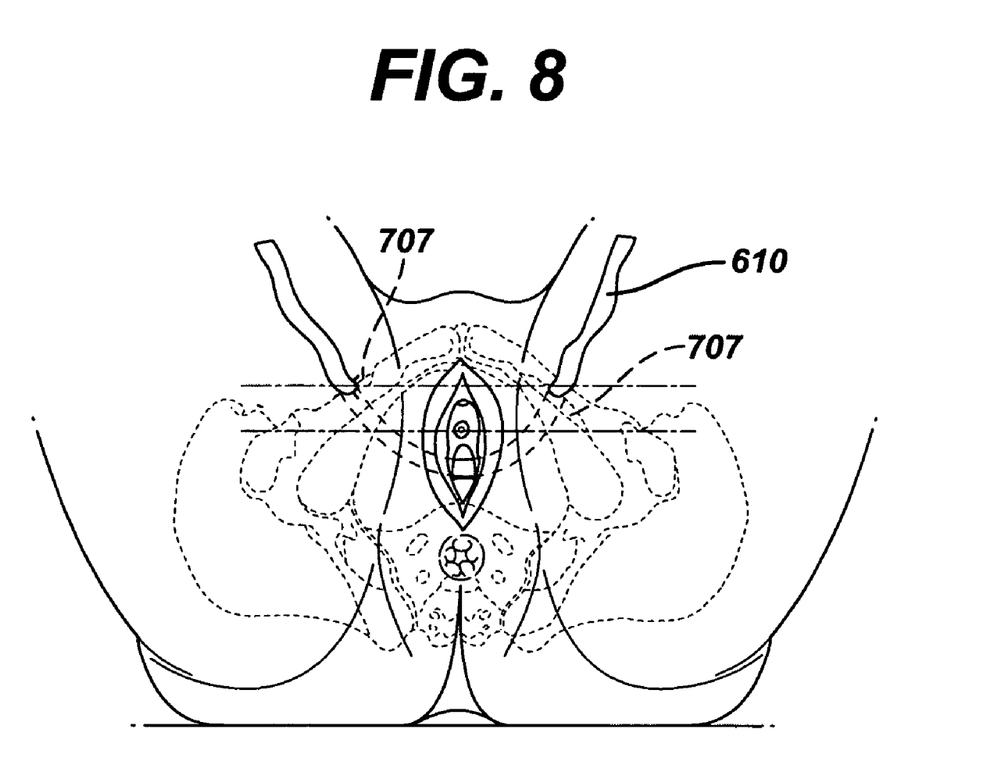

Referring once again to the procedure, once the guide element is fully inserted on one side as described above, the surgical passer 602 with associated tube element 606 for that side of the body is then inserted. The assembly is positioned within the C-shaped stem portion and passed through the dissected tract following the channel of the stem portion of the guide element from the vaginal incision and through the obturator membrane. Once the tip of the assembly traverses the obturator membrane, the guide element is removed. The assembly is rotated the remainder of the way through until the tip emerges from the skin at the exit point. The end of the tube element is then grasped, and the surgical passer reverse rotated to bring it back through the dissected tract and out through the vaginal incision. Subsequently, the tube element is pulled through the skin incision until the tape 610 exits the skin incision. The process is then repeated on the patient's other side and the tape adjusted, leaving the tape to form the sub-urethral sling beneath the mid-portion of the urethra as shown in FIG. 8.

Thus, with the aid of the guide device of the present invention, the procedure described above can be performed more safely and efficiently. The guide element ensures that the surgical assembly remains clear of any organs and nerves, while its configuration ensures its own safety by utilizing extensions to prevent over-insertion. Further, the above-described guide element is versatile enough to be used with any patient.

The above-described guide is preferably made using a unique stamping technology developed specifically for this application. Manufacturing processes that utilize stamping are well known. In general, a dye having the shape of the desired product "stamps" a sheet of metal to cut or punch the desired shape out of the metal. Stamping stainless steel produces sharp burrs around the edges that must be removed, particularly when the end product is a surgical device such as the present guide element. Stamping annealed stainless steel is even more difficult, as the softer the grade the more difficult burrs are to control given the gummy nature of the annealed stainless steel. The guide of the present invention requires a somewhat softer grade of stainless steel to allow the movable portions of the extensions to be bent (sometimes repeatedly) without breaking off.

Known tumbling, bead blasting, or chemical treatments are commonly used to remove burrs. Such treatments, however, tend to distort other product features. It is particularly important to avoid such distortion in the areas of the hinges. Hand removal techniques are labor intensive and expensive. Thus, known manufacturing techniques fail to offer a reliable and efficient way to use stamping technology to manufacture the above-described guides. Accordingly, a new stamping technique was developed that enables production of nearly burr-free stainless steel guides.

Figure 9A:
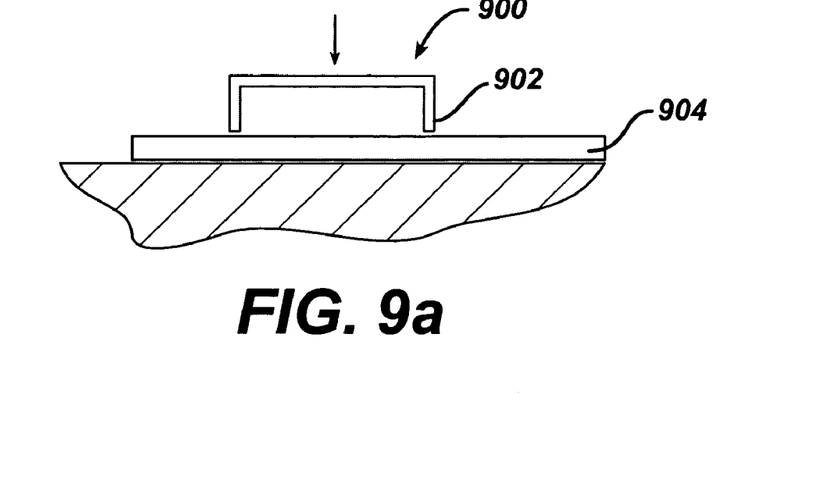
FIGS. 9a–9c illustrate steps in a method for manufacturing a guide according to the present invention.
Figure 9B:
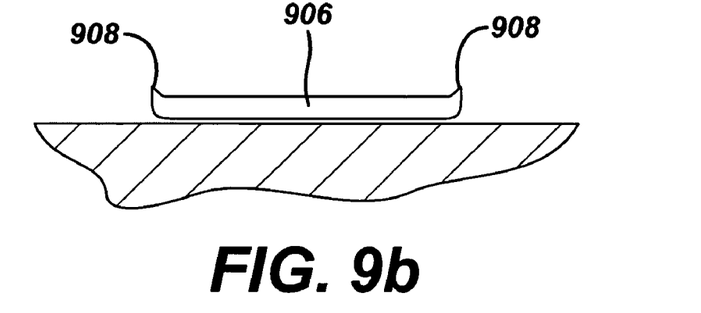
Figure 9C:
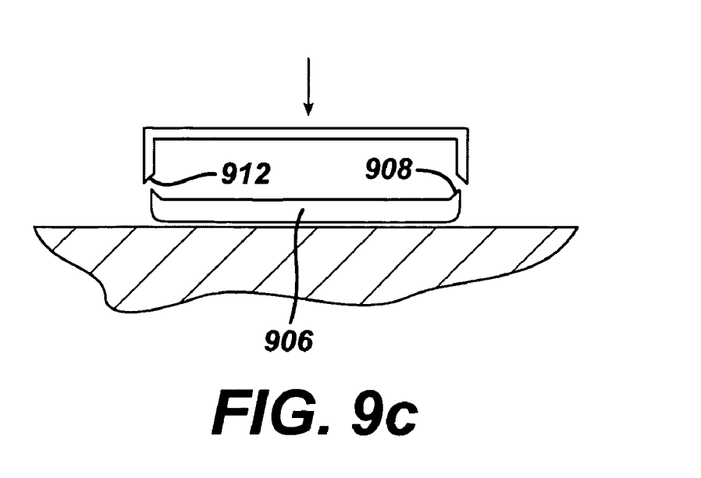

This new technique involves first using traditional stamping techniques and dyes to produce an initial specimen from which the burrs must be removed. A first dye 900 (FIG. 9a) having standard blunt edges 902 and having a circumferential configuration substantially corresponding to the desired shape of the guide is brought down against the stainless steel sheet 904 in the direction shown by the arrow to punch out the initial guide specimen. Subsequently, the specimen 906 is turned over so that the side with the burrs is facing upward, as is illustrated in FIG. 9b. Next, a second dye is used to "reverse stamp" the specimen. This second dye 910 has substantially the same circumferential configuration as the first dye, but has a leading edge 912 that is angled, preferably at 45 degrees, rather than blunt. It has been found that this procedure results in a substantially burr-free specimen. Very small remaining burrs must still be removed by conventional methods (i.e., chemical processing), but such post-processing now requires much shorter cycle times. Thus, the manufacturing process is faster and less expensive, and importantly, is less likely to weaken the product or otherwise degrade its properties.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A guide for use in medical procedures, comprising:
a stem portion extending substantially along a longitudinal axis between a proximal end and a distal end, and having a cross-sectional shape having a recess therein along its length; and
first and second extension portions extending outwardly from opposites sides of the distal end of the stem portion, each of said first and second extension portions further comprising a stationary portion that is fixedly coupled to the stem portion and has a substantially planar configuration extending outwardly from the stem portion and a movable portion that has a substantially planar configuration and is movably coupled to the stationary portion substantially only along a line that is substantially perpendicular to the longitudinal axis of the stem and extends along at least a portion of a proximal edge of the stationary portion, the movable portions being movable relative to the respective stationary portions by pivoting about said substantially perpendicular line between a first position wherein the stem portions extend beyond the extension portions by a first distance and the stationary and movable portions lie in substantially the same plane, and a second position wherein the stem portions extend beyond the extension portions by a second distance that is greater than the first distance.

2. The guide according to claim 1, wherein when the extension portions are in the first position the length of the stem portion that extends beyond the extension portions is approximately 55–65 mm, and wherein when the extension portions are in the second position the length of the stem portion that extends beyond the extension portions is approximately 65–75 mm.

3. The guide according to claim 1, wherein the cross-section of the stem portion is substantially C-shaped.

4. The guide according to claim 1, wherein the extension portion further comprises a plurality of gripping elements.

5. The guide according to claim 1, wherein for each extension portion, the movable portion is bendably coupled to the stationary portion.

6. The guide according to claim 1, wherein for each extension portion, the movable portion is pivotably coupled to the stationary portion.

7. The guide according to claim 1, wherein the first and second extension portions extend outwardly from opposite sides of the stem portion to form an angle therebetween of approximately 135 to 180 degrees.

8. The guide according to claim 1, wherein the first and second extension portions extend outwardly from opposite sides of the stem portion to form an angle therebetween of approximately 45 to 135 degrees.

9. A guide for use in a medical procedure to treat female urinary incontinence, said medical procedure involving the use of one or more surgical needles coupled to a tape to be implanted as support for the patient's urethra, the guide comprising:
   a stem portion extending substantially along a longitudinal axis between a proximal end and a distal end and having a cross-section having a recess therein along its longitudinal axis, the recess being shaped to receive therein said one or more surgical needles; and
   first and second extension portions extending outwardly from opposites sides of the distal end of the stem portion, each of said first and second extension portions further comprising a stationary portion that is fixedly coupled to the stem portion and has a substantially planar configuration extending outwardly from the stem portion, and a movable portion that has a substantially planar configuration and is movably coupled to the stationary portion substantially only along a line that is substantially perpendicular to the longitudinal axis of the stem and extends along at least a portion of a proximal edge of the stationary portion, the movable portions being movable relative to the respective stationary portions by pivoting about said substantially perpendicular line between a first position wherein the stationary and movable portions lie in substantially the same plane and the stem portions extend beyond the extension portions by a first distance, and a second position wherein the stem portions extend beyond the extension portions by a second distance that is greater than the first distance.

10. The guide according to claim 9, wherein in the second position the movable portion is positioned substantially parallel and adjacent to the stationary portion.

11. The guide according to claim 9, wherein the first distance is approximately 55–65 mm and the second distance is approximately 65–75 mm.

12. The guide according to claim 9, wherein the first and second extension portions extend outwardly from opposite sides of the stem portion to form an angle therebetween of approximately 135 to 180 degrees.

13. The guide according to claim 9, wherein the first and second extension portions extend outwardly from opposite sides of the stem portion to form an angle of approximately 45 to 135 degrees.

* * * * *